United States Patent [19]
Miller

[11] Patent Number: 6,053,968
[45] Date of Patent: Apr. 25, 2000

[54] PORTABLE ROOM AIR PURIFIER

[76] Inventor: Bob C. Miller, 8601 SE. Bristol Way, Jupiter, Fla. 33458

[21] Appl. No.: 09/172,319

[22] Filed: Oct. 14, 1998

[51] Int. Cl.$^7$ ....................................................... A61L 9/20
[52] U.S. Cl. ................................... 96/224; 96/16; 96/223
[58] Field of Search ............................... 96/16, 223, 224; 422/121, 24; 219/724; 250/438

[56] References Cited

U.S. PATENT DOCUMENTS

| | | | |
|---|---|---|---|
| 3,750,370 | 8/1973 | Brauss et al. | 96/224 |
| 4,210,429 | 7/1980 | Golstein | 96/224 |
| 4,621,195 | 11/1986 | Larsson | 250/438 |
| 4,672,160 | 6/1987 | Katoh | 219/724 |
| 5,185,015 | 2/1993 | Searle | 96/224 |
| 5,330,722 | 7/1994 | Pick et al. | 96/224 |
| 5,523,057 | 6/1996 | Mazzilli | 96/224 |
| 5,601,786 | 2/1997 | Monagan | 96/224 |
| 5,656,242 | 8/1997 | Morrow et al. | 96/224 |

*Primary Examiner*—David A. Simmons
*Assistant Examiner*—Minh-Chau T. Pham
*Attorney, Agent, or Firm*—McHale & Slavin

[57] ABSTRACT

A portable room air filter includes a rigid housing having an essentially-hollow reflective interior chamber. The interior chamber is bounded at one end by an air exhaust port, and by a removable HEPA filter element in fluid communication with an air intake port at an opposite, second end. The air purifier includes a germicidal ultraviolet light source mounted within the interior chamber, and a fan assembly draws air through the purifier. Baffling constructions prevent escape of ambient ultraviolet light, while ensuring free airflow through the purifier. Separate power switches control the fan assembly and ultraviolet light source. The purifier includes an interlock switch that disables the fan and ultraviolet light source when the purifier is opened. A status indicator provides visual feedback regarding the state of the ultraviolet light source. The purifier is lightweight and includes a grasping handle to facilitate movement of the purifier as needed.

7 Claims, 4 Drawing Sheets

PORTABLE ROOM AIR PURIFIER

FIELD OF THE INVENTION

This invention is directed to air purifiers and particularly to a lightweight, portable, single-room air purifier having unique safety-increasing features.

BACKGROUND OF THE INVENTION

Airborne irritants can be distributed in the home or workplace. These irritants can include, among other things, molds, pollen, bacteria, dust, and viruses. The spread of these particles can produce serious reactions among those who are sensitive. Even among those who are less-sensitive, longterm exposure to contaminated air may cause respiratory or other health problems. Breathing cleaner air generally leads to improved health.

In recognition of the relationship between clean air and improved health, several types of air purifiers have been developed. U.S. Pat. No. 5,435,817 issued to Davis et al., discloses a portable room air purifier that uses a HEPA filter to remove airborne irritants. The Davis device includes spiraled discharge scrolls that distribute air uniformly around the device. The Davis device does not kill pathogens collected on the HEPA filter element; micro-organisms can continue to grow once trapped. Furthermore, extremely-small organisms, like viruses, may pass directly through a HEPA filter element.

Other devices use ultraviolet (UV) light to kill pathogens. In some instances, UV lamps are placed directly within the ductwork of central air conditioning units. These devices are designed to expose air passing through the duct to shortwave UV light, typically 254 nm. This wavelength is destructive to the DNA of many micro-organisms. As a result, shortwave UV light has germicidal effects. Repeated or prolonged exposure to this type of UV light can significantly reduce live bacteria, mold spores, and virus levels in treated air. Unfortunately, while duct-mounted UV lamps may improve the air quality in some buildings, these devices require specialized installation. Also, the units may not be readily transferred from one building to another.

Some portable air purifiers, like that disclosed by U.S. Pat. No. 4,017,736 have been designed to incorporate shortwave UV light. Unfortunately, exposure to shortwave UV light can produce negative side effects. The human eye is particularly sensitive to shortwave UV light. Exposure to shortwave UV light may, for example, cause an inflammatory eye condition known as photokeratitis, which may cause pain and sensitivity to light. Louvered openings, perforated screens, and filter elements are not effective in visually blocking light from an ultraviolet light source.

A portable device that includes a shortwave UV light source must also include safety features that reduce the likelihood of unwanted exposure to UV light. Some UV-including air purifiers rely on shutoff switches to disable UV lamps if the device is opened. Although shutoff switches prevent direct UV exposure when a device is open, they do not reduce exposure to ambient UV light that may leak through inlet or outlet ports while the device is operating. Other UV-including devices cover inlet or outlet ports with mesh screens to reduce ambient UV light exposure. Although filter screens may reduce exposure to ambient UV light, prolonged exposure to the area around these screens is still not recommended. These screens also reduce airflow efficiency. Additionally, these screens are only effective when installed correctly. A screen that has been removed for cleaning may not be reseated properly. In other situations, inlet and outlet screens may be removed in an attempt to increase airflow through the device. Operating a UV-including purifier with ill-fitting, or missing, filter screens may produce unacceptable levels of exposure to shortwave UV light. Ironically, many UV-including devices may eliminate one type of problem only to create others.

Thus, what is needed is a portable room air purifier that includes advantages of the known devices, while addressing the shortcomings they exhibit. The air purifier should include a High Efficiency Particulate Air (HEPA) filter and a germicidal shortwave UV light source. The air purifier should also include safety features that allow safe usage of the device in all environments, including those in which curious children present. The air purifier should also include features that promote free airflow, regardless of the location of the purifier within a given room. The purifier should be compact and easily transported from one room to another, as needed. The device should also be lightweight enough to be placed on a variety of supporting surfaces.

SUMMARY OF THE INVENTION

The instant invention is a low cost portable room air purifier that combines enhanced safety features with improved air flow characteristics. The purifier includes a rigid housing having an essentially-hollow, reflective interior. An ultraviolet light source cooperates with the reflective interior and strategically-located panels to fill the purifier interior with direct and reflected ultraviolet light. A High Efficiency Particulate Air (HEPA) filter, including a washable pre-filter removably mounted within the purifier removes 99.97% of particles that are 0.3 microns or larger. The HEPA filter is germicidally treated by light from the ultraviolet light source. The baffle constructions eliminate leakage of ambient ultraviolet light and ensure that airflow through the purifier is not governed by the position of the device within a given room. Separate power switches allow independent control of a motor-driven fan and the ultraviolet lamps. An emergency interlock device disables the ultraviolet lamps when the purifier is open. The purifier is lightweight and includes a grasping handle to facilitate movement from one location to another.

Thus, it is an objective of the instant invention to provide an air purifier that combines a HEPA filter with a shortwave UV light source in a unit that may be operated safely, particularly around inquisitive children.

An additional objective of the instant invention is to provide an air purifier that eliminates ambient ultraviolet light leakage and maintains high flowthrough rates, regardless of position within a given room.

Yet another objective of the instant invention is to provide an air purifier that is compact and portable.

Still an additional objective of the instant invention is to provide an air purifier that is lightweight and inexpensive.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENT

Figure 1:
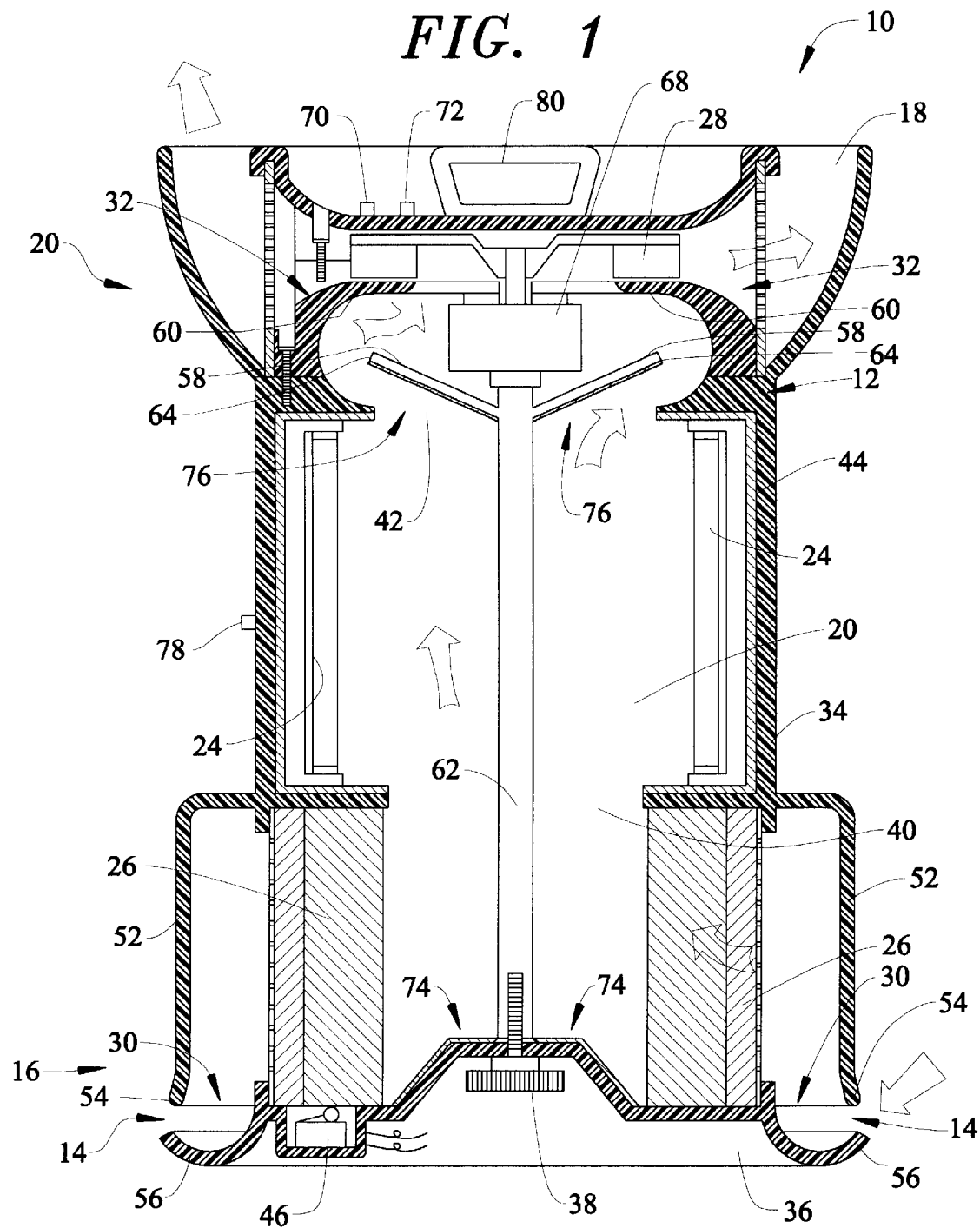
FIG. 1 is a cross-section view of the air purifier of the present invention.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown in the drawings and described in the specification.

Figure 4:
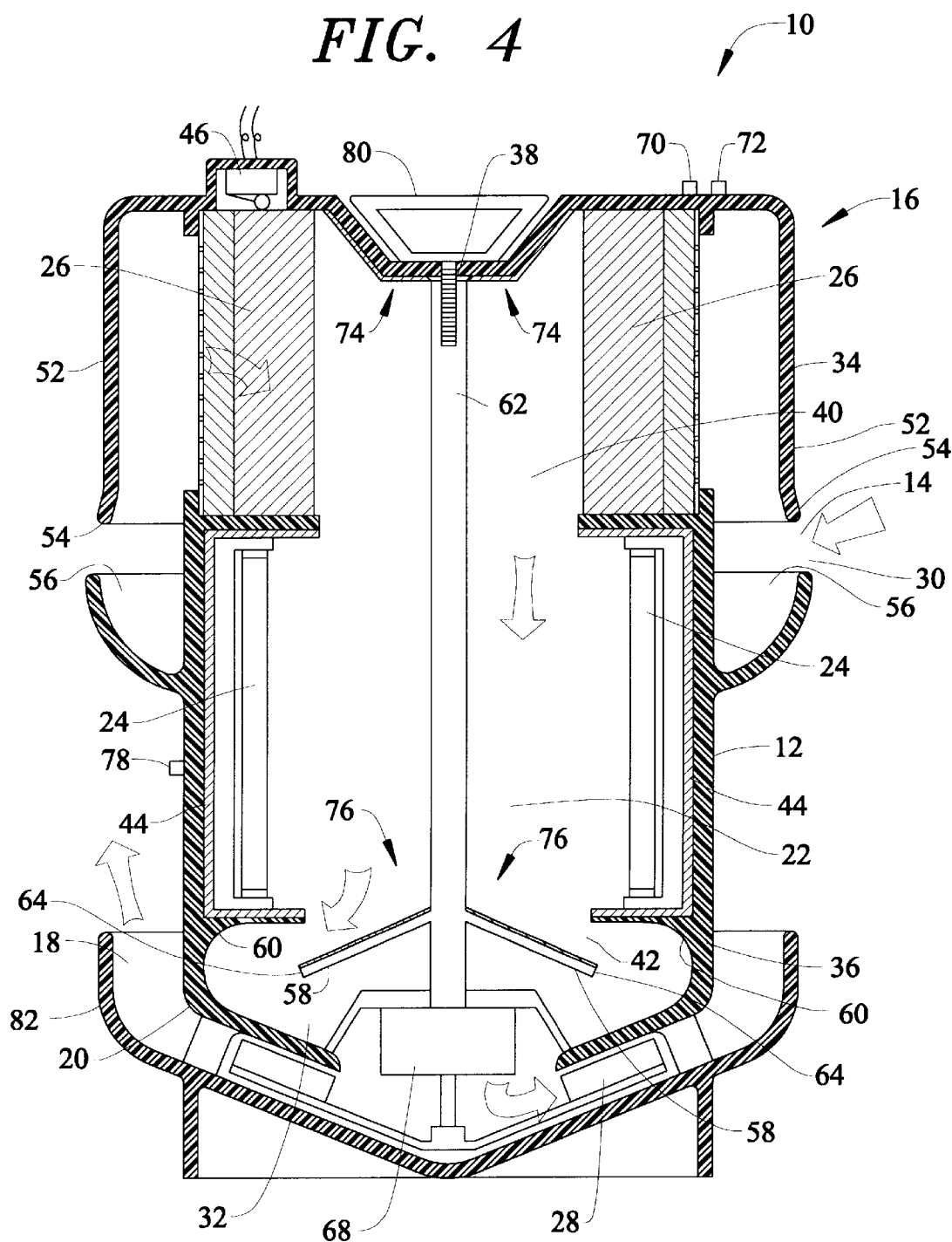
FIG. 4 is a cross-section view of another embodiment of the air purifier of the present invention.

Now with reference to FIG. 4, the air purifier 10 according to the present invention is shown. By way of overview, the air purifier 10 comprises an essentially-cylindrical housing 12 having an air inlet port 14 at a first end 16 and an air exhaust port 18 at an opposite second end 20. The housing 12 is characterized by an interior chamber 22 located therein. An ultraviolet light source 24 is disposed within the interior chamber 22. A High Efficiency Particulate Air filter (HEPA) filter 26 is removably mounted between the air intake port 14 and the interior chamber 22. Air is directed through the purifier 10 by an electric fan 28. The fan 28 draws air into the purifier 10 through the intake port 14 and forces the air out through the air exhaust port 18. In keeping with the safety-promoting objectives of the present invention, the purifier 10 advantageously includes first and second baffle constructions 30,32 that prevent internal ultraviolet light from reaching the area surrounding the purifier, while ensuring unrestricted airflow inflow and outflow.

With continued reference to FIG. 4, the purifier housing 12 comprises two portions 34,36 that are releasably joined together. More particularly, the housing first portion 34 is the upper body of the purifier 10; the housing second portion 36 is a contoured base plate that steadies the purifier during use. As will be described more fully below, the base plate 36 not only provides a resting surface for the purifier 10, it is also a part of the first light-blocking construction 30. The housing portions 36,38 are detachably joined together by a central, threaded thumbscrew 38. Separating the base plate 36 from the housing upper body 34 provides access to the HEPA filter 26 mounted inside the purifier 10, allowing the filter to be replaced as needed.

With continued reference to FIG. 4, the purifier interior chamber 22 is an essentially-hollow region within the purifier housing 12. The interior chamber 22 includes an entrance 40 oriented toward the air intake port 14 and an exit 42 oriented toward the air exhaust port 18. Two ultraviolet light tubes 24 bathe the interior chamber 22 with shortwave germicidal ultraviolet light. The surface 44 of the interior chamber 22 is reflective. The reflective nature of the chamber surface 44 effectively increases the intensity of ultraviolet light within the interior chamber 22. With the present arrangement, even extremely small pathogens, are killed as air passes through the chamber 22, on the way from the intake port 14 to the air exhaust port 18. The HEPA filter 26 is continually exposed to ultraviolet light, killing bacteria and other irritants trapped therein. Although the preferred embodiment of the purifier 10 includes two UV light tubes 24, other more, or fewer, may be used if desired.

To help meet the increased safety goals of the present invention, the purifier 10 includes unique features which ensure that the purifier 10 does not transmit ultraviolet light into the surrounding area. With reference to FIG. 4, the purifier includes an automatic shutoff device 46 that prevents operation of the ultraviolet light source 24 and fan 28 if the purifier housing 12 is opened. More specifically, power to the ultraviolet light bulbs 24 and fan motor 68 is governed by a spring-loaded switch 46 that electrically connects the first and second housing portions 34,36. If the housing portions 34,36 are separated, the shutoff switch 46 interrupts power to the ultraviolet light bulbs 24 and motor 68.

The shutoff interlock 46 is supplemented by a pair of novel, multi-function baffle constructions 30,32. These baffle constructions 30,32 not only prevent unwanted ultraviolet light escape, they allow unrestricted airflow through the device. The first baffle construction 30 is associated with the air intake port 14. As seen in FIG. 4, the first baffle construction 30 includes a blocking shell 52 that circles the lower portion of the purifier 10. The blocking shell 52 has a contoured distal edge 54 disposed in a nested arrangement with the housing second portion or base plate 36. The perimeter of the base plate 36 includes a curved flange 56 having a U-shaped cross section. The curved flange 56 forms a valley into which the distal edge 54 of the blocking shell 52 extends. This shell-and-flange nesting arrangement prevents individuals who use this purifier 10 from looking inside the device. The first baffle construction 30 keeps ultraviolet light from escaping through the air intake port, even if the device 10 is operated without a HEPA filter 26 in place. However, the shell distal edge 54 is advantageously spaced apart from the curved flange 56. This spacing allows air intake from around the entire circumference of the purifier 10.

The circumferential nature of the air intake port 14 also allows the purifier 10 to be effective regardless of placement within a room. Furthermore, the flared nature of the first baffle construction 30 ensures that air intake is not impeded even if the purifier 10 is placed in a corner or against a wall. As a result, the purifier 10 of the present invention works equally well when placed in a corner, against a wall, or in the center of a room. The housing 12 may, however, have a cross-section that is not round, if desired. Additionally, although the air exhaust port 18 may be located at various locations along the height of the housing 12, a top mounted exhaust port is preferred.

As mentioned above, the purifier 10 also includes a second baffle construction 32 associated with the air exhaust port 18. The second baffle construction 32 prevents ultraviolet light from escaping through the air exhaust port 18. Like the first baffle construction 30, which prevents ultraviolet light leakage past through the air intake port 14, the second baffle construction 32 prevents ultraviolet light leakage. The second baffle construction 32 employs cooperating elements 58,60 to prevent unwanted exposure to ultraviolet light. As seen in FIG. 1, the second baffle construction 60 includes a blocking wall 58 mounted on a central shaft 62 that extends longitudinally within the interior chamber 22. The blocking wall 58 has a distal edge 64 positioned so that the blocking wall cooperates with a curved blocking trough 60 to prevent ambient ultraviolet light from traveling past the air exhaust port 18 and into the surrounding area.

In combination, the shutoff switch 46 and the baffle constructions 30,32 provide a multi-faceted approach for preventing unwanted exposure to ultraviolet light. As a result, the purifier 10 of the present invention safely combines the germicidal benefits produced by ultraviolet light, while maintaining efficient flowthrough.

Airflow through the purifier 10 is produced by a centrifugal fan 28 powered by an corresponding electric motor 68.

Figure 2:
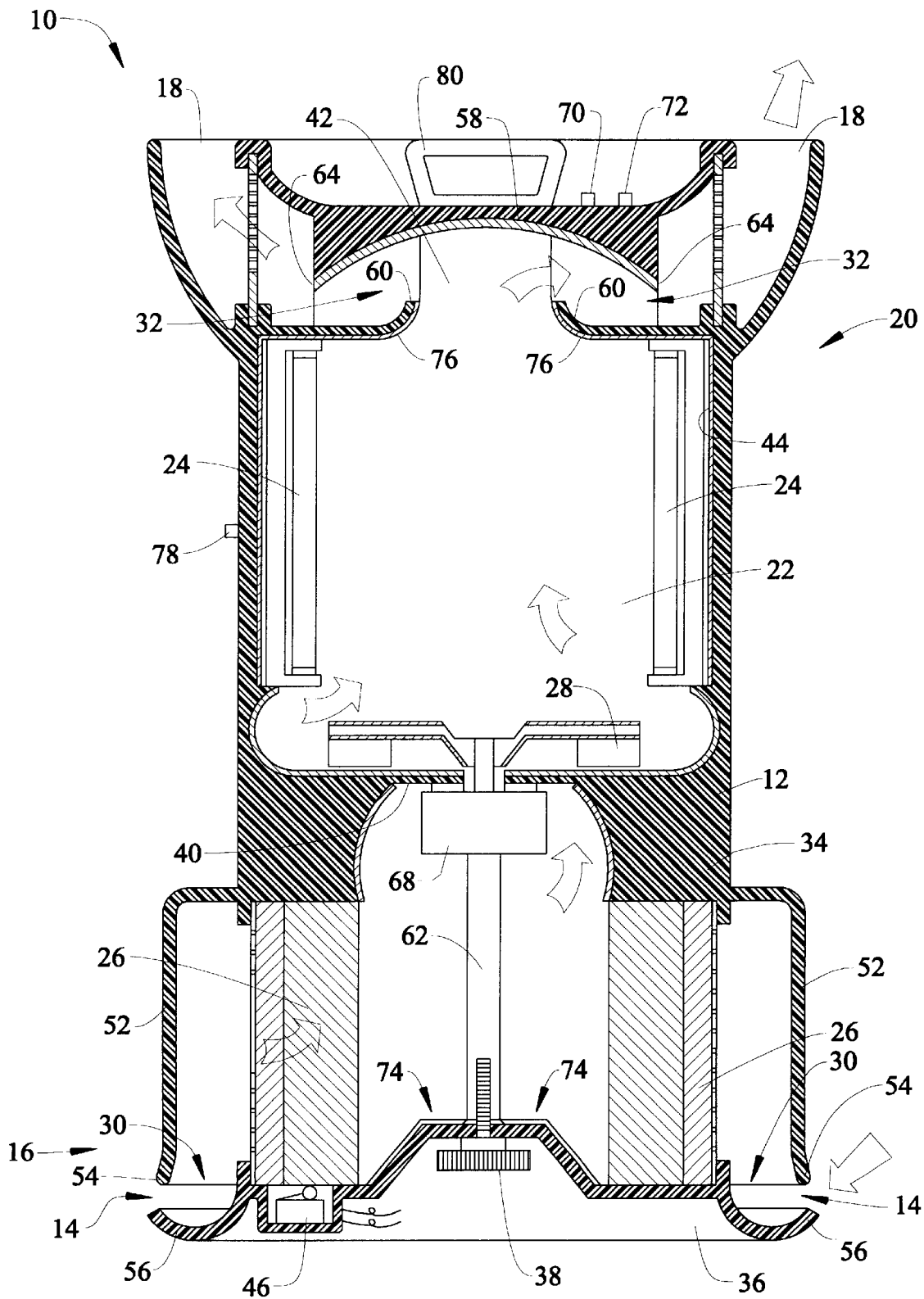
FIG. 2 is a cross-section view of an alternate embodiment of the air purifier of the present invention.
Figure 3:
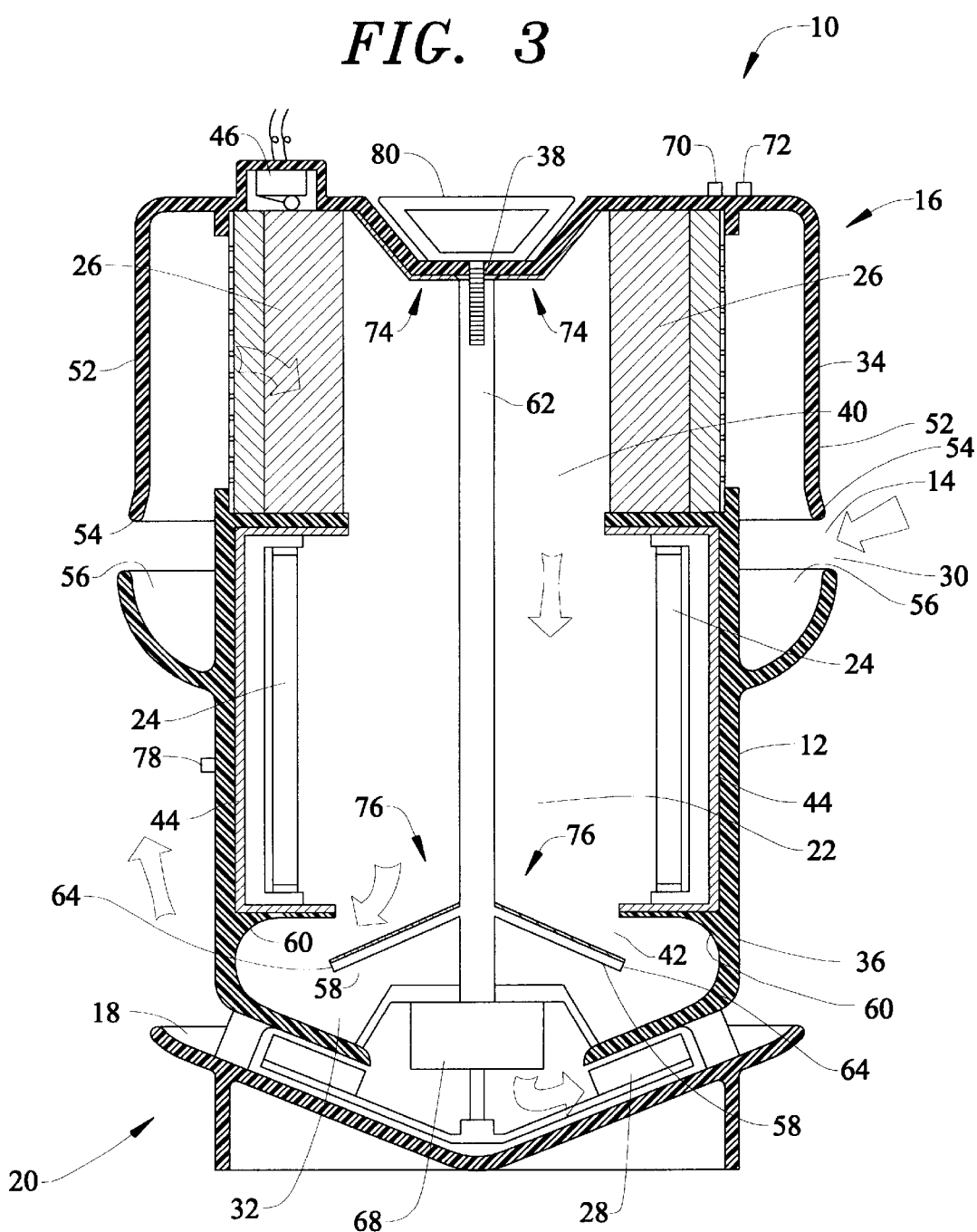
FIG. 3 is a cross-section view of an additional embodiment of the air purifier of the present invention.

As seen in FIG. 4, the motor 68 and fan 28 are mounted between the second baffle construction 60 and the central shaft 62. In a preferred embodiment, the fan 28 is positioned between the interior chamber exit 42 and the air exhaust port 18. The position of the fan 28 and motor 68 within the housing 12 is not critical, however; several other orientations are possible. As seen in FIG. 2, the fan 28 and motor 68 may be mounted in the middle of the purifier 10. FIG. 3 shows that the fan 28 and motor 68 may also be located at the bottom of the purifier 10. Additionally, although the preferred embodiment employs a centrifugal fan 28 other types of fans would suffice to move air through the purifier 10.

During use, the fan 28 draws air in through the air intake port 14, pulling the air through the HEPA filter 26, where 99.97% of particles 0.03 microns or larger are trapped. These particles include pollen, molds, bacteria, and dust. After passing through the HEPA filter 26, the air continues into the interior chamber 22, where it is bombarded by ultraviolet radiation from the ultraviolet light bulbs 24 disposed therein. Exposure to this light kills microorganisms that may have passed through the HEPA filter, including viruses.

To increase the effectiveness of the included ultraviolet lights 24, the purifier 10 also includes reflective panels 74,76 located at strategic locations within the device. The first panel 74 is mounted adjacent the HEPA filter element 26, reflecting ultraviolet light directly onto the HEPA filter. As a result, the first panel 74 cooperates with the germicidal ultraviolet lights to sanitize the HEPA filter element 26, killing germs trapped therein. The second reflective panel 76 is located near the exit 42 of the interior chamber 22. In a preferred embodiment, the second reflective panel 76 is integrated into the blocking wall 58 of the second baffle construction 32. With this arrangement, the second baffle construction 32 serves several purposes. The baffle construction 32 makes the purifier increasingly safe, by preventing ultraviolet light leakage, more effective, by reflecting ultraviolet light back into the interior chamber 22, and more efficient, by ensuring non-restricted air output.

As an additional safety feature, the purifier 10 includes an ultraviolet light status indicator 78. In a preferred embodiment, the indicator 78 is a light-transmitting fiber optic cable passing through the housing 12 and extending into the interior chamber 22. The indicator 78 is optically shielded to prevent direct exposure to ultraviolet light.

The ultraviolet lights 24 and motor 68 are controlled by separate power switches 70,72. In this way, the lights 24 and fan 28 may be operated independently. This allows the fan 28 to be turned off without requiring that the ultraviolet lights 24 also be turned off. This separate switch arrangement not only allows continual ultraviolet sanitizing of the HEPA filter 26, it also increases the useful life of the ultraviolet bulbs 24. Ultraviolet bulbs 24 perform best when allowed to operate continuously. Conversely, subjecting the bulbs 24 to repeated on/off cycles reduces bulb life. The employment of separate power switches 70,72 allows users of the present invention to conserve energy by turning off power to the fan motor 68, while enjoying the long bulb life benefits produced by continuous bulb operation and simultaneously preventing organism growth within the device and filter elements.

In keeping with the portable nature of the invention, the purifier 10 includes a grasping handle 80 located at the top of the housing 12. The handle 80 allows the purifier 10 to be moved easily from one location to another as needed.

For certain allergy sufferers, it is important not to stir up floor-based irritants. For use in these situations, an alternate embodiment of the device, shown in FIG. 4, includes an airflow deflector 82. The airflow deflector 82 is juxtaposed with the air exhaust port 18 and directs discharged air upward, away from the support surface, not shown, on which the purifier 10 is placed during use.

Although the invention has been described in terms of a specific embodiment, it will be readily apparent to those skilled in this art that various modifications, rearrangements and substitutions can be made without departing from the spirit of the invention. The scope of the invention is defined by the claims appended hereto.

What is claimed is:

1. A lightweight, portable room air purification device comprising:

a multi-part cylindrical housing assembly having an upper portion and a lower portion, operable when in a joined orientation, having an ultraviolet purification section and a particle filtration section;

said ultraviolet purification section including an internal reflective chamber, an air exhaust port at a first end, an air intake port at a second end, and ultraviolet light for irradiation of said internal reflective chamber, said air exhaust port constructed and arranged to transfer air from within said reflective chamber in an arc measuring substantially three hundred sixty degrees with respect to a central axis of said housing assembly, and said air intake port constructed and arranged to transfer air into said reflective chamber through an arc measuring substantially three hundred sixty degrees with respect to said central axis of said housing assembly;

said particle filtration section including a HEPA filtration device releasably positioned between said reflective chamber and said air intake means for retention of particulate matter therein, said HEPA filtration device being irradiated by said ultraviolet light source during use;

an air circulation assembly defined by an electrically operated motor and fan in fluid communication with said housing assembly for maintaining air flow therethrough;

first and second baffling means each respectively juxtaposed with one of said ports and operative to provide ultraviolet light dispersion for destruction of airborne organisms, and to prevent UV light from being visible outside of said housing, said first baffling means including a blocking shell extending from a lower circumferential edge of said upper portion, and a substantially-U-shaped flange extending from an upper circumferential edge of said lower portion, said blocking shell and flange constructed and arranged in a nested relationship effective to block UV radiation passage therethrough, said second baffling means including a blocking wall that extends radially within said housing chamber, and a contoured blocking trough constructed and arranged to cooperate in a nested arrangement with said blocking wall effective to prevent UV radiation passage therethrough; and a safety interlock device constructed and arranged so as to prevent operation of the device when said housing assembly is in a disassembled orientation.

2. The room air purification device of claim 1, further including:

means for indicating operational status of said ultraviolet light source, said means for indicating disposed within said housing.

3. A lightweight, portable room air purifier comprising:

a cylindrical housing assembly having an upper portion and a lower portion, operable when in a joined orientation, said assembly including a first piece and a second piece, said housing assembly having an interior including an ultraviolet purification section and a particle filtration section;

said particle filtration section further including a HEPA filtration device releasably positioned between said reflective chamber and said air intake means for retention of particulate matter therein;

said ultraviolet purification section including an internal reflective chamber having an entrance and an exit; and a source of ultraviolet light for irradiation of said internal reflective chamber and said HEPA filtration device;

said housing assembly having a first end including an air intake port in fluid communication with said chamber entrance; and air exhaust port in fluid communication with said chamber exit, said air intake port constructed and arranged to transfer air into said reflective chamber through an arc measuring substantially three hundred sixty degrees with respect to said central axis of said housing assembly, and said air exhaust port constructed and arranged to transfer air from within said reflective chamber in an arc measuring substantially three hundred sixty degrees with respect to a central axis of said housing assembly;

an air circulation assembly defined by an electrically operated motor and fan in fluid communication with said housing assembly for maintaining air flow therethrough;

first and second baffling means respectively juxtaposed with said air inlet means and said air exhaust means and operative to provide ultraviolet light dispersion for destruction and removal of airborne particles;

said first baffling means including a blocking shell extending from a lower circumferential edge of said upper portion, and a substantially-U-shaped flange extending from an upper circumferential edge of said lower portion, said blocking shell and flange constructed and arranged in a nested relationship effective to block UV radiation passage therethrough;

said second baffling means including a blocking wall that extends radially within said housing chamber, and a contoured blocking trough constructed and arranged to cooperate in a nested arrangement with said blocking wall effective to prevent UV radiation passage therethrough;

an interlock device electrically connecting said housing first piece and said second piece, said switch preventing operation of said ultraviolet light source and said fan while said first piece is separated from said second piece;

an ultraviolet light source use indicator disposed within said housing;

a power switch for operating said ultraviolet light source; and a power switch for operating said circulation assembly; whereby a compact air purifier simultaneously provides improved safety features and increased airflow.

4. The room air purification device of claim 3 further including at least one reflective panel disposed within said housing.

5. The room air purification device of claim 4 further including an airflow deflector to direct discharged air away from a support surface on which said housing assembly is placed during use.

6. The room air purification device of claim 4 further including a grasping handle extending from said housing.

7. The room air purification device of claim 4 further including an activated charcoal filter element constructed and arranged to remove odor from air flowing through said air exhaust means.

* * * * *